(12) United States Patent  
Wiederin et al.

(10) Patent No.: US 9,146,182 B1  
(45) Date of Patent: Sep. 29, 2015

(54) INJECTION VALVE

(71) Applicant: Elemental Scientific, Inc., Omaha, NE (US)

(72) Inventors: Daniel R. Wiederin, Omaha, NE (US); Nathan Saetveit, Omaha, NE (US)

(73) Assignee: Elemental Scientific, Inc., Omaha, NE (US)

( * ) Notice: Subject to any disclaimer, the term of this patent is extended or adjusted under 35 U.S.C. 154(b) by 30 days.

(21) Appl. No.: 14/163,311

(22) Filed: Jan. 24, 2014

Related U.S. Application Data (60) Provisional application No. 61/759,549, filed on Feb. 1, 2013.

(51) Int. Cl.
| | |
|---|---|
| *F16K 11/074* | (2006.01) |
| *G01N 30/20* | (2006.01) |
| *G01N 1/28* | (2006.01) |

(52) U.S. Cl.
CPC .............. *G01N 1/28* (2013.01); *G01N 2030/201* (2013.01); *G01N 2030/202* (2013.01); *G01N 2030/207* (2013.01); *Y10T 137/86863* (2015.04)

(58) Field of Classification Search
CPC ................. Y10T 137/86863; G01N 2030/201; G01N 2030/202; G01N 2030/207
USPC .................................................... 137/625.46
See application file for complete search history.

(56) References Cited

U.S. PATENT DOCUMENTS

| | | | | | |
|---|---|---|---|---|---|
| 3,192,954 | A | * | 7/1965 | Gerhold et al. | 137/625.11 |
| 4,068,528 | A | * | 1/1978 | Gundelfinger | 73/864.84 |
| 4,444,066 | A | * | 4/1984 | Ogle et al. | 73/863.72 |
| 5,105,851 | A | * | 4/1992 | Fogelman | 137/625.11 |
| 5,848,611 | A | * | 12/1998 | Stanevich | 137/625.47 |
| 5,920,006 | A | * | 7/1999 | Zelechonok | 73/61.56 |
| 6,012,487 | A | * | 1/2000 | Hauck | 137/625.11 |
| 6,502,448 | B1 | * | 1/2003 | Rapkin | 73/1.03 |
| 8,241,013 | B2 | * | 8/2012 | Moeller et al. | 417/286 |

\* cited by examiner

*Primary Examiner* — John Fox
(74) *Attorney, Agent, or Firm* — Advent, LLP (57) ABSTRACT

Valve assemblies are described that provide flow paths in substantially indirect opposition for fluids injected into the valve assemblies for mixing. A valve assembly includes a first valve member having ports configured to receive a first fluid and a second fluid. The valve assembly also includes a second valve member coupled adjacent to the first valve member. The valve assembly defines a first flow path for the first fluid and a second flow path for the second fluid. The first flow path extends from one of the ports of the first valve member toward an interface between the first valve member and the second valve member, and the second flow path extends from a channel defined by the second valve member toward the interface between the first valve member and the second valve member. The second flow path is in substantially indirect opposition to the first flow path.

20 Claims, 6 Drawing Sheets

INJECTION VALVE

CROSS-REFERENCE TO RELATED APPLICATIONS

The present application claims the benefit under 35 U.S.C. §119(e) of U.S. Provisional Application Ser. No. 61/759,549, filed Feb. 1, 2013, and titled "INJECTION VALVE," which is herein incorporated by reference in its entirety.

BACKGROUND

Inductively Coupled Plasma (ICP) spectrometry is an analysis technique commonly used for the determination of trace element concentrations and isotope ratios in liquid samples. ICP spectrometry employs electromagnetically generated partially ionized argon plasma which reaches a temperature of approximately 7,000K. When a sample is introduced to the plasma, the high temperature causes sample atoms to become ionized or emit light. Since each chemical element produces a characteristic mass or emission spectrum, measuring the spectra of the emitted mass or light allows the determination of the elemental composition of the original sample.

Sample introduction systems may be employed to introduce the liquid samples into the ICP spectrometry instrumentation (e.g., an Inductively Coupled Plasma Mass Spectrometer (ICP/ICP-MS), an Inductively Coupled Plasma Atomic Emission Spectrometer (ICP-AES), or the like) for analysis. For example, a sample introduction system may withdraw an aliquot of a liquid sample from a container and thereafter transport the aliquot to a nebulizer that converts the aliquot into a polydisperse aerosol suitable for ionization in plasma by the ICP spectrometry instrumentation. The aerosol is then sorted in a spray chamber to remove the larger aerosol particles. Upon leaving the spray chamber, the aerosol is introduced into the plasma by a plasma torch assembly of the ICP-MS or ICP-AES instruments for analysis.

SUMMARY

Valve assemblies are described that provide flow paths in substantially indirect opposition for fluids injected into the valve assemblies for mixing. A valve assembly includes a first valve member having ports configured to receive a first fluid and a second fluid. The valve assembly also includes a second valve member coupled adjacent to the first valve member. The valve assembly defines a first flow path for the first fluid and a second flow path for the second fluid. The first flow path extends from one of the ports of the first valve member toward an interface between the first valve member and the second valve member, and the second flow path extends from a channel defined by the second valve member toward the interface between the first valve member and the second valve member. The second flow path is in substantially indirect opposition to the first flow path.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

DETAILED DESCRIPTION

Overview

Figure 1:
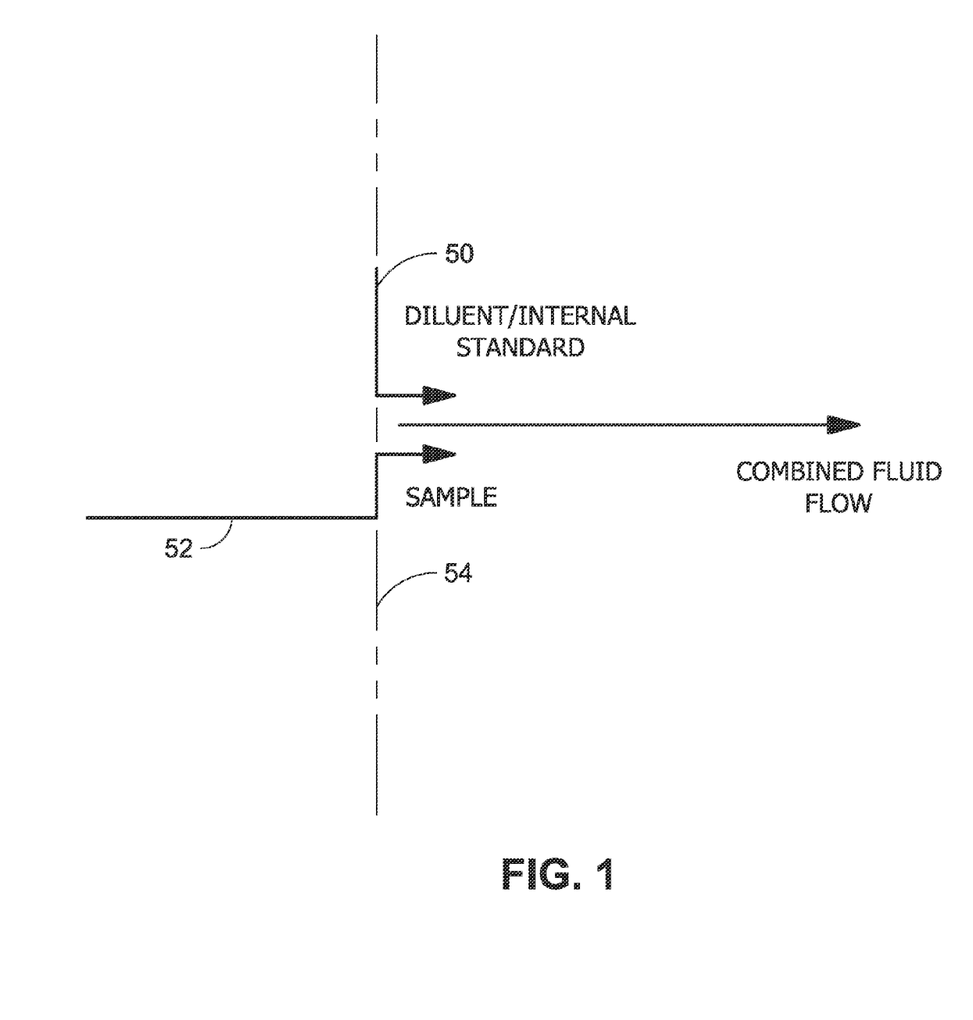
FIG. 1 is a partial diagrammatic illustration of a multiport valve configuration where a sample fluid and a diluent/internal standard meet in direct opposition for mixing.

Multiport valves are typically used to transport sample materials to laboratory equipment for analysis. For example, multiport valves can be used to introduce liquid samples into ICP spectrometry instrumentation for analysis. Multiport valves can also be used to load samples on columns for liquid and/or gas chromatography. Typical valves used in these applications include six-port (6-port), two-position (2-position) rotary valves. Generally, two ports of a rotary valve are connected to an external (sample) loop, one port is connected to a sample source, another port is connected to a carrier source, a further port is connected to a vent (waste), and another port is connected to a nebulizer/column. When the valve is in a first orientation, sample from the sample source flows through the sample loop, while carrier from the carrier source flows directly to a nebulizer/column. When the valve is rotated to a second orientation, the carrier source is connected to the sample loop for injecting the sample contained in the sample loop into the nebulizer or onto the column. In some multiport valve configurations, one fluid is mixed with another fluid by injecting the two fluids into separate ports of a multiport valve. In these configurations, the two fluids meet along flow paths in direct opposition. For example, a diluent/internal standard 50 and a sample 52 are injected into a multiport valve so that the two fluids meet along flow paths 54 in direct opposition.

Valve assemblies are described that provide flow paths in substantially indirect opposition for fluids injected into the valve assemblies for mixing. In some embodiments, a valve assembly includes a first valve member (e.g., a stator) having ports configured to receive a first fluid (e.g., a diluent and/or an internal standard) and a second fluid (e.g., a sample fluid). The ports are configured to connect to an external loop (e.g., a sample loop), an output (e.g., a nebulizer, a column, and so forth), and a vent (e.g., waste). The valve assembly also includes a second valve member (e.g., a rotor) coupled adjacent to the first valve member. The second valve assembly defines channels configured to connect the external loop to the second fluid in one orientation (e.g., rotational position) for charging the external loop with the second fluid, and to connect the external loop to the output in another orientation (e.g., rotational position) for supplying the second fluid from the external loop to the output. The valve assembly defines a first flow path for the first fluid and a second flow path for the second fluid. The first flow path extends from one of the ports of the first valve member toward an interface between the first valve member and the second valve member, and the second flow path extends from a channel defined by the second valve member toward the interface between the first valve member and the second valve member. The second flow path is in substantially indirect opposition to the first flow path.

Example Implementations

Figure 2A:
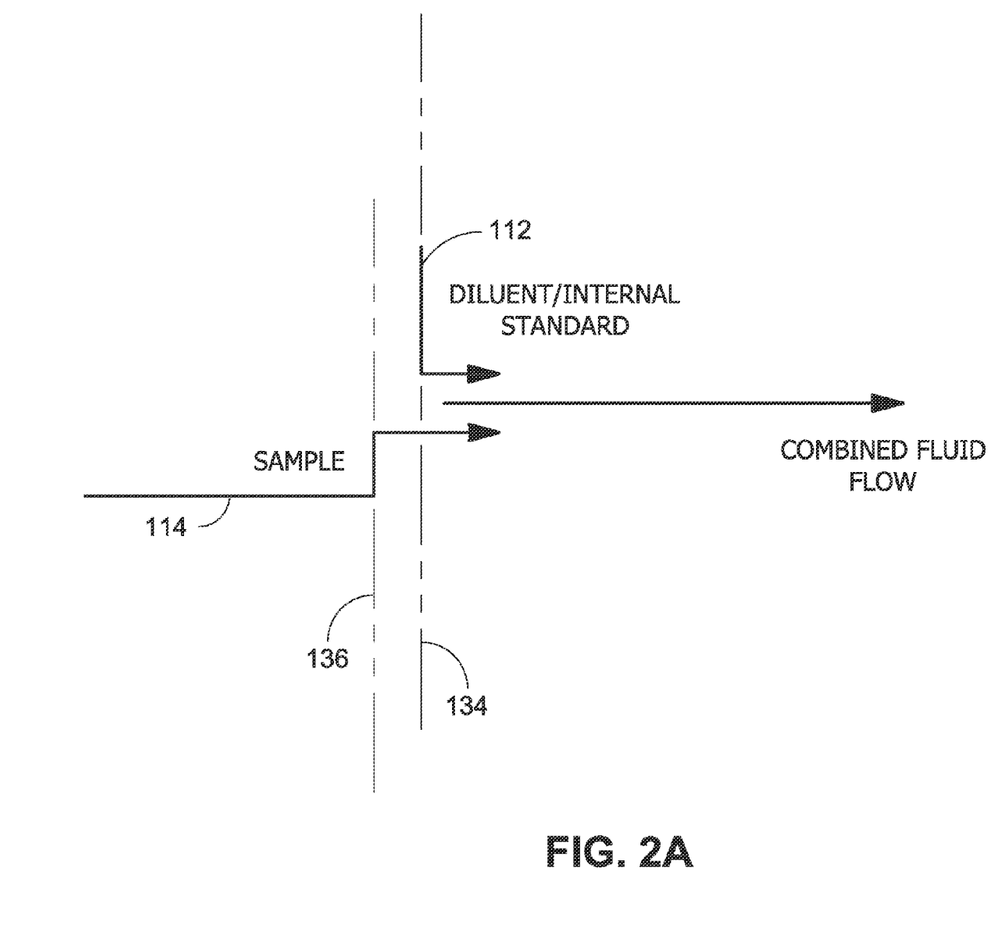
FIG. 2A is a partial diagrammatic illustration of a multiport valve configuration where a sample fluid and a diluent/internal standard meet along flow paths in substantially indirect opposition for mixing in accordance with example implementations of the present disclosure.
Figure 2B:
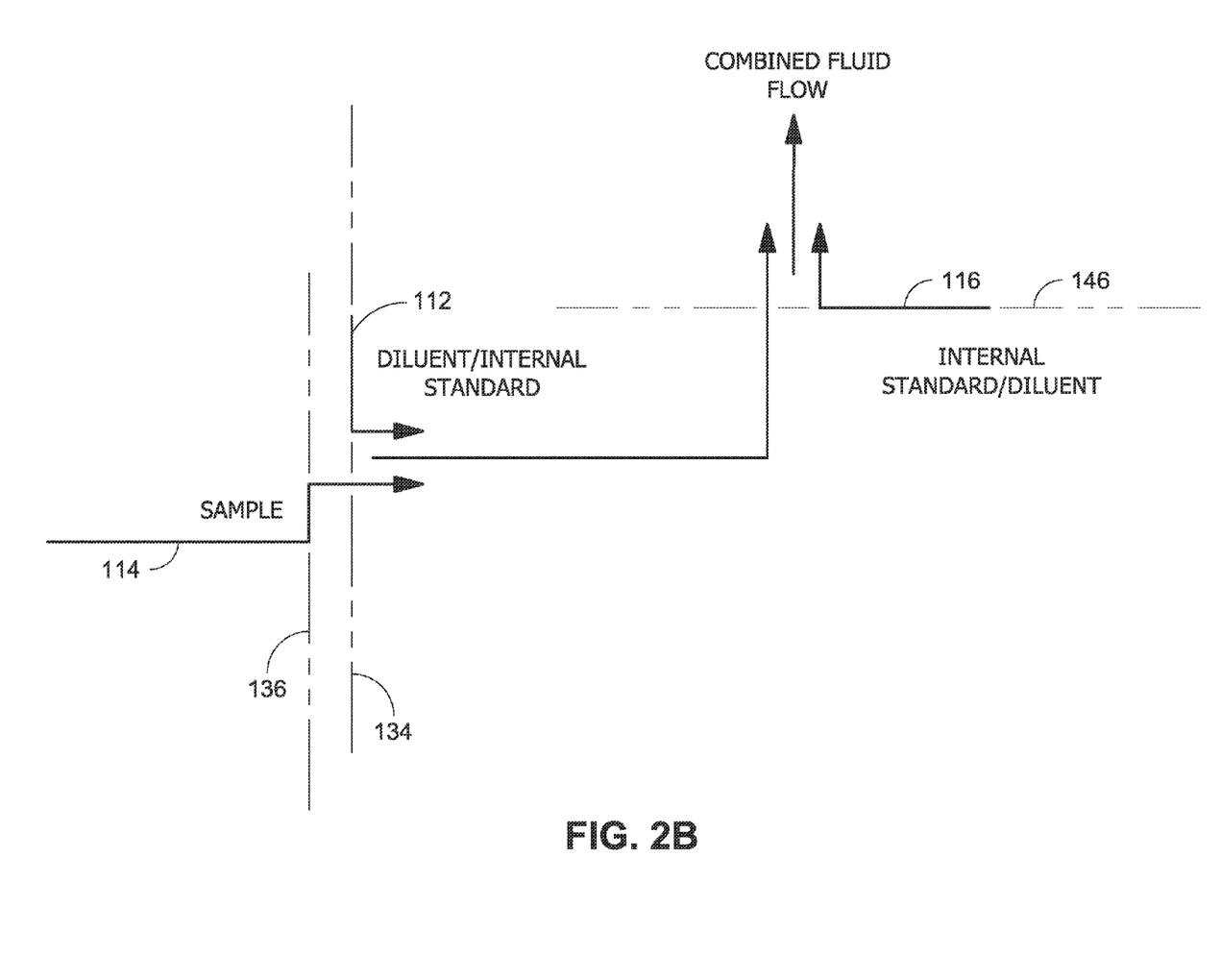
FIG. 2B is a partial diagrammatic illustration of a multiport valve configuration where a sample fluid and a diluent/internal standard meet along flow paths in substantially indirect opposition for mixing, and where an internal standard/diluent is further mixed with the combined fluid flow of the sample fluid and the diluent/internal standard in accordance with example implementations of the present disclosure.
Figure 3:
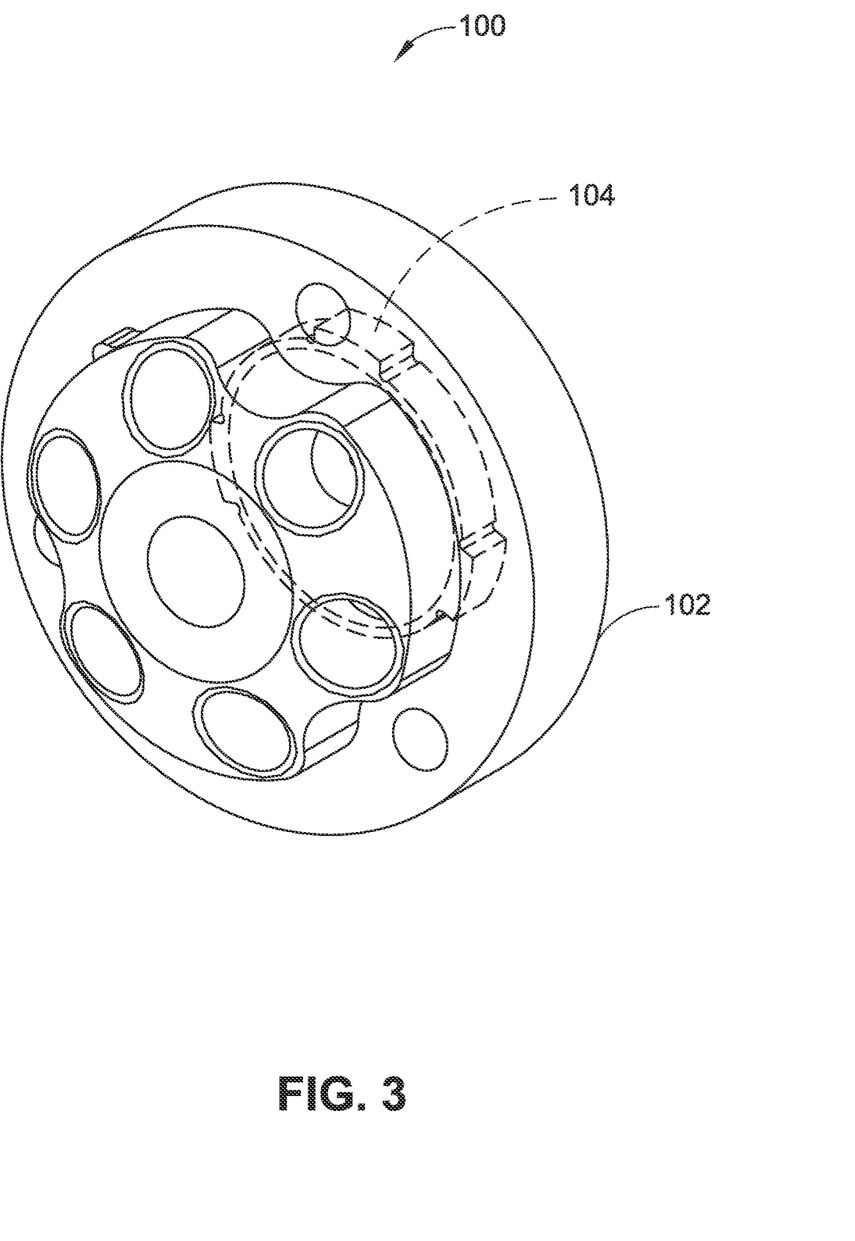
FIG. 3 is an isometric view illustrating a multiport flow valve assembly including a stator and a rotor configured to provide flow paths in substantially indirect opposition for fluids injected into the valve assembly for mixing in accordance with example implementations of the present disclosure.
Figure 4A:
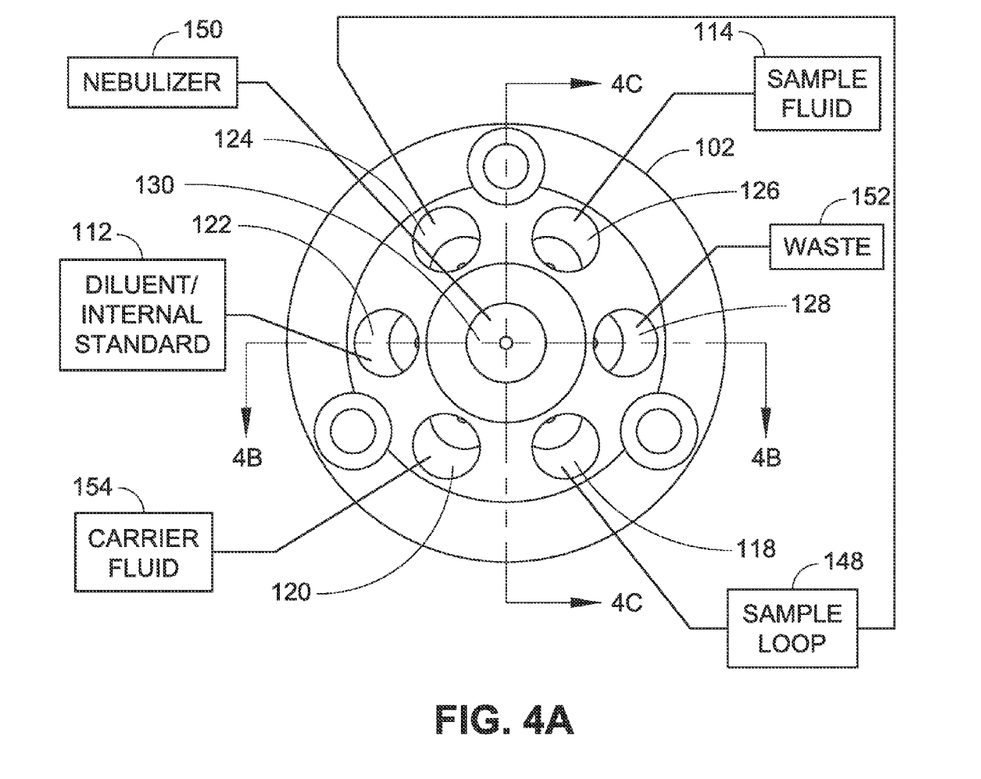
FIG. 4A is a top plan view of a multiport flow valve stator head with flow paths in substantially indirect opposition for fluids injected into the valve assembly for mixing in accordance with example implementations of the present disclosure.
Figure 4B:
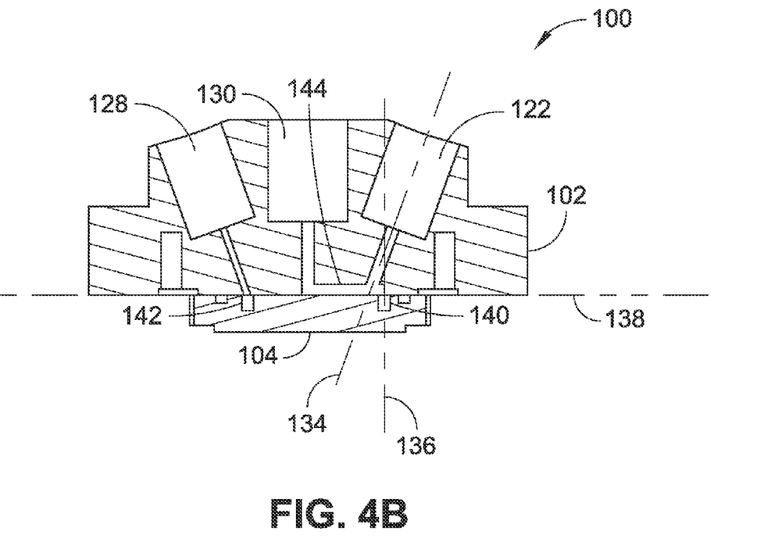
FIG. 4B is a cross-sectional side elevation view of the stator head illustrated in FIG. 4A, further illustrating a rotor interfacing with the stator to form a multiport flow valve assembly in accordance with example implementations of the present disclosure.
Figure 4C:
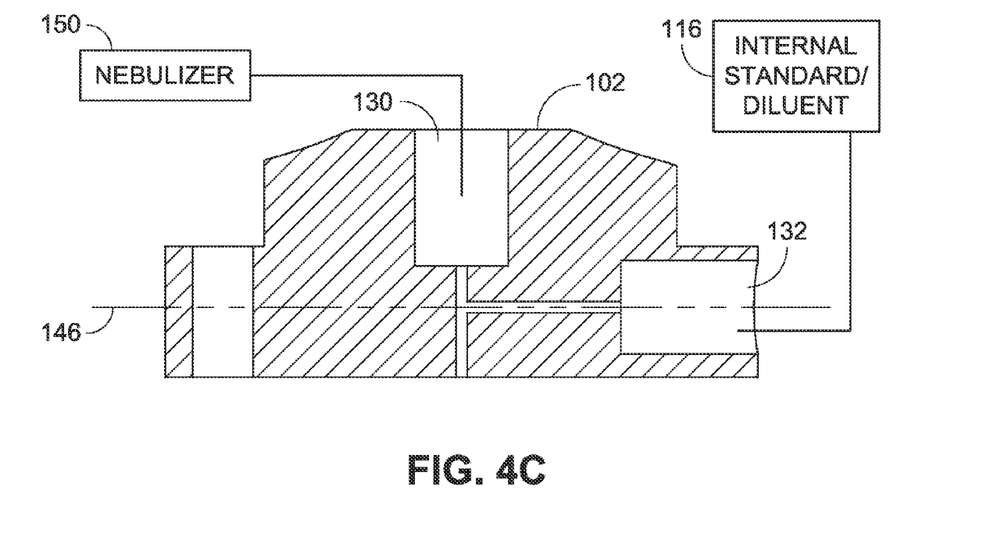
FIG. 4C is another cross-sectional side elevation view of the stator head illustrated in FIG. 4A.
Figure 4D:
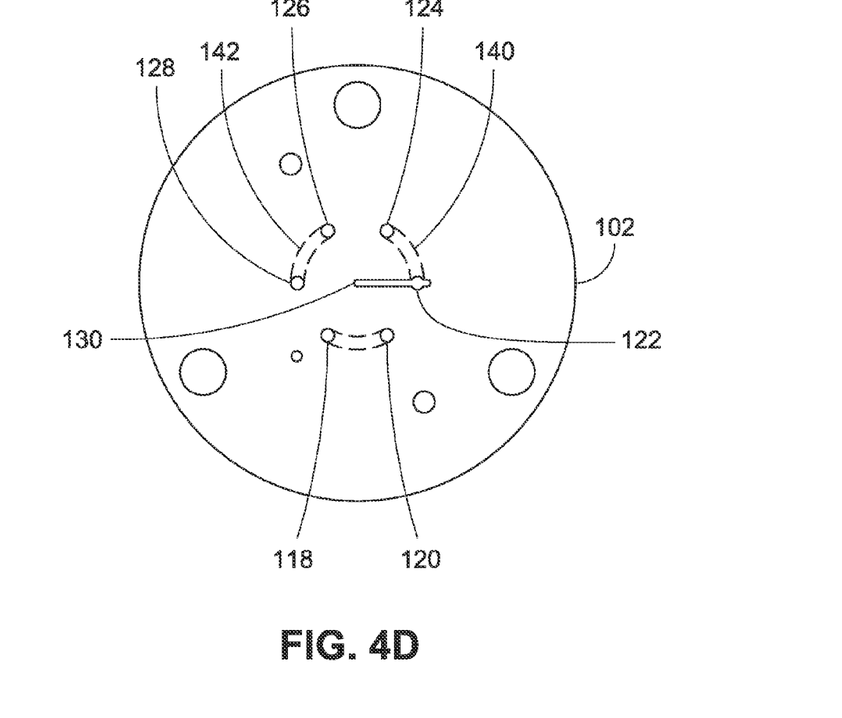
FIG. 4D is a bottom plan view of the stator head illustrated in FIG. 4A.

FIGS. 2 through 4 illustrate an example stator 102 and an example rotor 104 for a valve assembly 100. The valve assembly 100 includes a first valve member and a second valve member coupled adjacent to the first valve member. As shown, the valve assembly 100 can be configured as a rotary valve assembly having a first valve member comprising a stator 102 and a second valve member comprising a rotor 104 coupled adjacent to the stator 102 so that it can rotate with respect to the stator 102. The valve assembly 100 is configured to furnish a high degree of mixing between two or more fluids (e.g., a sample fluid and a diluent and/or an internal standard) supplied to instrumentation, such as ICP spectrometry instrumentation, and so forth. In implementations, the valve assembly 100 provides a high degree of mixing at high dilution factors (DF), and can provide more reproducible stabilization times (e.g., for ICP spectrometry) at various dilution factors. It should be noted that while the accompanying figures show the stator 102 and the rotor 104 of the valve assembly 100, the valve assembly 100 may also include additional components, such as components for holding the rotor 104 adjacent to the stator 102, and so forth. For example, the valve assembly 100 may further include a drive configured to rotate the rotor 104 and/or the stator 102, and a housing configured to support the stator 102 and/or the rotor 104 adjacent to the stator 102.

The stator 102 includes ports configured to connect to an external loop (e.g., a sample loop 148), an output (e.g., a nebulizer 150), and a vent/waste 152. The stator 102 is configured to receive a first fluid (e.g., a carrier fluid 154), a second fluid (e.g., a sample fluid 114), a third fluid (e.g., a diluent/internal standard 112), and/or a fourth fluid (e.g., an internal standard/diluent 116). The stator 102 includes a first port 118 configured to connect to the sample loop 148, a second port 120 configured to receive the carrier fluid 154, a third port 122 configured to receive the diluent/internal standard 112, a fourth port 124 configured to connect to the sample loop 148, a fifth port 126 configured to receive the sample fluid 114, a sixth port 128 configured to connect to waste 152, and/or a seventh port 130 configured to connect to the nebulizer 150. In implementations, the stator 102 may also include an eighth port 132 configured to connect to the nebulizer 150. The eighth port 132 may be positioned in the side of the stator 102 to furnish online dilution of, for example, the sample fluid 114. For instance, a source of internal standard/diluent 116 can be connected to the eighth port 132, and the internal standard/diluent 116 can be supplied while the sample fluid 114 and/or the diluent/internal standard 112 is pumped to the nebulizer 150. The eighth port 132 may also be used to provide a rinse for rinsing the connection to the nebulizer 150. In implementations, the stator 102 may also include a drain port, which may be connected to a channel in the rotor 104. In implementations, fluid flow to the ports of the stator 102 can be controlled using an instrument such as a valve controller (not shown).

The rotor 104 includes channels configured to connect the sample loop 148 to the sample fluid 114 in a first (load) orientation for charging the sample loop 148 with the sample fluid 114, and to connect the sample loop 148 to the nebulizer 150 in a second (inject) orientation for supplying the sample fluid 114 from the sample loop 148 to the nebulizer 150. For example, the rotor 104 includes a first channel configured to connect the second port 120 to the third port 122 in the first orientation, and to connect the first port 118 to the second port 120 in the second orientation. The rotor 104 also includes a second channel 140 configured to connect the fourth port 124 to the fifth port 126 in the first orientation, and to connect the third port 122 to the fourth port 124 in the second orientation. The rotor 104 further includes a third channel 142 configured to connect the sixth port 128 to the first port 118 in the first orientation, and to connect the fifth port 126 to the sixth port 128 in the second orientation for supplying the sample fluid 114 from the sample loop 148 to the nebulizer 150.

The valve assembly 100 defines a flow path 134 for the diluent/internal standard 112 and a flow path 136 for the sample fluid 114. The flow path 134 extends from the third port 122 of the stator 102 toward an interface 138 between the stator 102 and the rotor 104. The flow path 136 extends from the second channel 140 of the rotor 104 toward the interface 138 between the stator 102 and the rotor 104. In embodiments of the disclosure, the flow path 134 is in substantially indirect opposition to the flow path 136. Further, the stator 102 includes a channel 144 configured to connect the flow path 134 to the seventh port 130. In some embodiments, the stator 102 also includes an eighth port 132 connected to the seventh port 130 to furnish online dilution of the sample fluid 114. For example, the internal standard/diluent 116 can be supplied to the eighth port 132 via a flow path 146 connecting the eighth port 132 to the seventh port 130.

It should be noted that while the terms "stator" and "rotor" are used herein to describe the first and second valve members, these terms are provided by way of example only (e.g., to illustrate how these components interface (e.g., rotate) with respect to one another), and are not meant to limit how the valve members can be actuated with respect to an external reference (e.g., valve mounting hardware, or the like). Thus, in one particular example, a component described as a "stator" may remain substantially stationary (e.g., with respect to an external reference, such as valve mounting hardware), and a component described as a "rotor" may rotate with respect to the stator. However, in another particular example, a component described as a "stator" may rotate with respect to a rotor, and a component described as a "rotor" may remain substantially stationary (e.g., with respect to valve mounting hardware). Further, in some implementations, both a component described as a "stator" and a component described as a "rotor" may rotate with respect to an external reference.

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A valve assembly comprising:
   a first valve member having a plurality of ports configured to receive a first fluid and a second fluid; and
   a second valve member coupled adjacent to the first valve member, the valve assembly defining a first flow path for the first fluid and a second flow path for the second fluid, the first flow path extending from one of the plurality of ports of the first valve member toward an interface between the first valve member and the second valve member, and the second flow path extending from a channel defined by the second valve member toward the interface between the first valve member and the second valve member, wherein the second flow path is in substantially indirect opposition to the first flow path.

2. The valve assembly as recited in claim 1, wherein the first valve member defines a channel configured to connect the first flow path to a second one of the plurality of ports of the first valve member.

3. The valve assembly as recited in claim 1, wherein the first valve member comprises a stator and the second valve member comprises a rotor coupled adjacent to the stator.

4. The valve assembly as recited in claim 1, wherein the plurality of ports is configured to connect to an external loop, an output, and a vent.

5. The valve assembly as recited in claim 4, wherein the second valve member defines a plurality of channels configured to connect the external loop to the second fluid in a first orientation for charging the external loop with the second fluid and to connect the external loop to the output in a second orientation for supplying the second fluid from the external loop to the output.

6. The valve assembly as recited in claim 4, wherein the external loop comprises a sample loop, the output comprises a nebulizer, the first fluid comprises at least one of a diluent or an internal standard, and the second fluid comprises a sample fluid.

7. The valve assembly as recited in claim 4, wherein the first valve member further comprises a port connected to one of the plurality of ports connected to the output to furnish online dilution of at least one of the first fluid or the second fluid.

8. A valve assembly comprising:
   a first valve member having a first port configured to connect to an external loop, a second port configured to receive a first fluid, a third port configured to receive a second fluid, a fourth port configured to connect to the external loop, a fifth port configured to receive a third fluid, a sixth port configured to connect to a vent, and a seventh port configured to connect to an output; and
   a second valve member coupled adjacent to the first valve member, the second valve member having a first channel configured to connect the second port to the third port in a first orientation for charging the external loop with the second fluid and to connect the first port to the second port in a second orientation for supplying the second fluid from the external loop to the output, a second channel configured to connect the fourth port to the fifth port in the first orientation and to connect the third port to the fourth port in the second orientation, a third channel configured to connect the sixth port to the first port in the first orientation and to connect the fifth port to the sixth port in the second orientation, the valve assembly defining a first flow path for the second fluid and a second flow path for the third fluid, the first flow path extending from one of the plurality of ports of the first valve member toward an interface between the first valve member and the second valve member, and the second flow path extending from a channel defined by the second valve member toward the interface between the first valve member and the second valve member, wherein the second flow path is in substantially indirect opposition to the first flow path.

9. The valve assembly as recited in claim 8, wherein the first valve member defines a channel configured to connect the first flow path to the seventh port.

10. The valve assembly as recited in claim 8, wherein the first valve member comprises a stator and the second valve member comprises a rotor coupled adjacent to the stator.

11. The valve assembly as recited in claim 8, wherein the external loop comprises a sample loop, the output comprises a nebulizer, the first fluid comprises a carrier fluid, the second fluid comprises at least one of a diluent or an internal standard, and the third fluid comprises a sample fluid.

12. The valve assembly as recited in claim 8, wherein the first valve member further comprises an eighth port connected to the seventh port to furnish online dilution of at least one of the first fluid or the second fluid.

13. A method comprising:
   receiving a sample fluid and at least one of a diluent or an internal standard at a valve assembly;
   connecting a sample loop to the sample fluid via the valve assembly in a first orientation for charging the sample loop with the sample fluid;
   connecting the sample loop to a nebulizer via the valve assembly in a second orientation for supplying the sample fluid from the sample loop to the nebulizer; and
   mixing the sample fluid and the at least one of the diluent or the internal standard by introducing the sample fluid and the at least one of the diluent or the internal standard in substantially indirect opposition.

14. The method as recited in claim 13, wherein the valve assembly comprises a first valve member having a plurality of ports configured to receive the sample fluid and the at least one of the diluent or the internal standard, and a second valve member coupled adjacent to the first valve member, the valve assembly defining a first flow path for the at least one of the diluent or the internal standard and a second flow path for the sample fluid.

15. The method as recited in claim 14, wherein the first flow path extends from one of the plurality of ports of the first valve member toward an interface between the first valve member and the second valve member, and the second flow path extends from a channel defined by the second valve member toward the interface between the first valve member and the second valve member.

16. The method as recited in claim 14, wherein the first valve member defines a channel configured to connect the first flow path to a second one of the plurality of ports of the first valve member.

17. The method as recited in claim 14, wherein the first valve member comprises a stator and the second valve member comprises a rotor coupled adjacent to the stator.

18. The method as recited in claim 14, wherein the plurality of ports is configured to connect to the sample loop, the output, and a vent.

19. The method as recited in claim 14, wherein the second valve member defines a plurality of channels configured to connect the sample loop to the second fluid in a first orientation for charging the external loop with the second fluid and to connect the sample loop to the nebulizer in a second orientation for supplying the second fluid from the external loop to the output.

20. The method as recited in claim 14, wherein the first valve member further comprises a port connected to one of the plurality of ports connected to the output to furnish online dilution of at least one of the first fluid or the second fluid.

* * * * *